US00PP21905P2

(12) United States Plant Patent
Schreurs

(10) Patent No.: US PP21,905 P2
(45) Date of Patent: May 3, 2011

(54) ***KNIPHOFIA* PLANT NAMED 'RED ROCKET'**

(50) Latin Name: *Kniphofia uvaria*
Varietal Denomination: Red Rocket

(75) Inventor: Pieter Schreurs, Stramproij (NL)

(73) Assignee: Compass Plants B.V., Hillegom (NL)

( * ) Notice: Subject to any disclaimer, the term of this patent is extended or adjusted under 35 U.S.C. 154(b) by 0 days.

(21) Appl. No.: 12/653,767

(22) Filed: Dec. 16, 2009

(51) Int. Cl.
*A01H 5/00* (2006.01)

(52) U.S. Cl. ..... Plt./443

(58) Field of Classification Search ..... Plt./443
See application file for complete search history.

*Primary Examiner* — June Hwu
(74) *Attorney, Agent, or Firm* — C. A. Whealy

(57) ABSTRACT

A new and distinct cultivar of *Kniphofia* plant named 'Red Rocket', characterized by its upright growth habit; moderately vigorous growth habit; early flowering habit; long flowering period; orange red-colored flowers; and good garden performance.

2 Drawing Sheets

Botanical designation: *Kniphofia uvaria.*
Cultivar denomination: 'RED ROCKET'.

BACKGROUND OF THE INVENTION

The present invention relates to a new and distinct cultivar of *Kniphofia* plant, botanically known as *Kniphofia uvaria* and hereinafter referred to by the name 'Red Rocket'.

The new *Kniphofia* plant is a naturally-occurring whole plant mutation of *Kniphofia uvaria* 'Nancy's Red', not patented. The new *Kniphofia* plant was discovered and selected by the Inventor as a single flowering plant within a population of plants of 'Nancy's Red' in a controlled greenhouse environment in Stramproij, The Netherlands in July, 2005.

Asexual reproduction of the new *Kniphofia* plant by tissue culture cuttings in a controlled environment in Lochristi, Belgium since July, 2006, has shown that the unique features of this new *Kniphofia* plant are stable and reproduced true to type in successive generations.

SUMMARY OF THE INVENTION

Plants of the new *Kniphofia* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Red Rocket'. These characteristics in combination distinguish 'Red Rocket' as a new and distinct cultivar of *Kniphofia:*

1. Upright growth habit.
2. Moderately vigorous growth habit.
3. Early flowering habit.
4. Long flowering period.
5. Orange red-colored flowers.
6. Good garden performance.

Plants of the new *Kniphofia* can be compared to plants of the parent, 'Nancy's Red'. Plants of the new *Kniphofia* differ from plants of 'Nancy's Red' in the following characteristics:

1. Plants of the new *Kniphofia* are stronger and healthier than plants of 'Nancy's Red'.

2. Plants of the new *Kniphofia* grow faster and flower earlier than plants of 'Nancy's Red'.

Plants of the new *Kniphofia* can also be compared to plants of *Kniphofia uvaria* 'Alcazar', not patented. In side-by-side comparisons conducted in Stramproij, The Netherlands, plants of the new *Kniphofia* differed from plants of 'Alcazar' in the following characteristics:

1. Plants of the new *Kniphofia* were shorter than plants of 'Alcazar'.
2. Plants of the new *Kniphofia* flowered for a longer period of time than plants of 'Alcazar'.
3. Plants of the new *Kniphofia* and 'Alcazar' differed in flower color as plants of 'Alcazar'.

BRIEF DESCRIPTION OF THE PHOTOGRAPHS

The accompanying colored photographs illustrate the overall appearance of the new *Kniphofia* plant, showing the colors as true as it is reasonably possible to obtain in colored reproductions of this type. Colors in the photographs may differ slightly from the color values cited in the detailed botanical description which accurately describe the colors of the new *Kniphofia* plant.

The photograph on the first sheet comprises a side perspective view of a typical plant of 'Red Rocket' grown in a container.

The photograph at the top of the second sheet is a close-up view of a typical inflorescence of 'Red Rocket'.

The photograph at the bottom of the second sheet is a close-up view of typical leaves of 'Red Rocket'.

DETAILED BOTANICAL DESCRIPTION

The aforementioned photographs and following observations, measurements and values describe plants grown in containers in an outdoor nursery in Stramproij, The Netherlands during the summer and under conditions which approximate commercial production. During the production of the plants, day temperatures ranged from 14° C. to 30° C. and night temperatures ranged from 7° C. to 14° C. Plants were two years old when the photographs and description were taken. In the following description, color references are made to The Royal Horticultural Society Colour Chart, 2007 Edition, except where general terms of ordinary dictionary significance are used.

Botanical classification: *Kniphofia uvaria* 'Red Rocket'.

Parentage: Naturally-occurring whole plant mutation of *Kniphofia uvaria* 'Nancy's Red', not patented.

Propagation:

*Type.*—By tissue culture.

*Time to initiate roots.*—About three weeks at 20° C.

*Time to produce a rooted young plant.*—About 45 days at 20° C.

*Root description.*—Thick, fibrous, fleshy; creamy yellow in color.

*Rooting habit.*—Freely branching; dense.

Plant description:

*Plant and growth habit.*—Herbaceous perennial; upright growth habit; basal rosette of leaves; flowering stems developing from the center of the basal rosette of leaves; moderately vigorous growth habit.

*Plant height, soil level to top of foliar plane.*—About 29.8 cm.

*Plant height, soil level to top of inflorescences.*—About 51.4 cm.

*Plant diameter.*—About 60.3 cm.

Foliage description:

*Arrangement.*—Alternate; simple; sessile.

*Length.*—About 36.6 cm.

*Width.*—About 7 mm.

*Shape.*—Lanceolate; strongly keeled.

*Apex.*—Long acuminate.

*Base.*—Broadly cuneate.

*Margin.*—Finely serrate; ciliate.

*Texture, upper and lower surfaces.*—Smooth, glabrous.

*Venation pattern.*—Parallel.

*Color.*—Developing leaves, upper and lower surfaces: Close to 144A to 144B; towards the base, close to 150B. Fully expanded leaves, upper surface: Close to 137B and 143A; towards the base, close to 143A; venation, close to 137B and 143A. Fully expanded leaves, lower surface: Close to 137B; towards the base, close to 143A to 143B; venation, close to 137B.

Flower description:

*Flower arrangement and habit.*—Single funnelform flowers arranged on upright terminal racemes; freely flowering habit with about 100 flowers per inflorescence; flowers face outwardly to downwardly.)

*Fragrance.*—None detected.

*Natural flowering season.*—Long flowering period, plants flower continuously from summer to early autumn in The Netherlands.

*Flower longevity.*—Individual flowers last about five days on the plant; flowers not persistent.

*Inflorescence height.*—About 18.3 cm.

*Inflorescence diameter.*—About 5 cm.

*Flower diameter.*—About 1 cm.

*Flower depth (height).*—About 2.9 cm.

*Flower bud.*—Length: About 1.6 cm. Diameter: About 3 mm. Shape: Narrowly oblong. Color: Close to 42B to 42C; towards the base, close to 34C to 34D.

*Corolla.*—Arrangement: Six segments fused towards the base into a tube; 20% of segments are free. Length: About 2.4 cm. Width: About 3 mm. Lobe shape: Ovate. Apex: Obtuse. Margin: Entire. Texture, upper and lower surfaces: Smooth, glabrous. Color: When opening, outer surface: Close to N34B to 42B to 42C. When opening, inner surface: Close to 31C and 32D. Fully opened, outer surface: Close to 31A; longitudinal stripes, close to 34A to 34B; color becoming closer to 35A with development. Fully opened, inner surface: Close to 25A.

*Sepals.*—None observed.

*Peduncles.*—Length: About 48.7 cm. Diameter: About 7 mm. Strength: Strong. Aspect: Erect to about 7.5° from vertical. Texture: Smooth, glabrous. Color: Close to 144A and 146A.

*Pedicels.*—Length: About 1.5 mm. Diameter: About 1 mm. Strength: Strong. Aspect: About 90° from vertical. Texture: Smooth, glabrous. Color: Close to 197A and N199A.

*Reproductive organs.*—Stamens: Quantity: About six per flower. Filament length: About 2.5 cm. Filament color: Close to 154B; towards the base, close to 150D. Anther shape: Oblong. Anther length: About 2 mm. Anther color: Close to N167A. Pollen amount: Scarce. Pollen color: Close to 8A to 8B. Pistils: Quantity: One per flower. Pistil length: About 2.4 cm. Style length: About 2.3 cm. Style color: Close to 153A to 153B. Stigma shape: Crested. Stigma color: Close to 22A. Ovary color: Close to 144B. Seed/fruit: Seed and fruit development have not been observed on plants of the new *Kniphofia*.

Garden performance: Plants of the new *Kniphofia* have been observed to have good garden performance and tolerate wind, rain and temperatures ranging from about −10° C. to about 40° C.

Pathogen/pest resistance: Plants of the new *Kniphofia* have not been observed to be resistant to pathogens and pests common to *Kniphofia*.

It is claimed:

1. A new and distinct *Kniphofia* plant named 'Red Rocket' as illustrated and described.

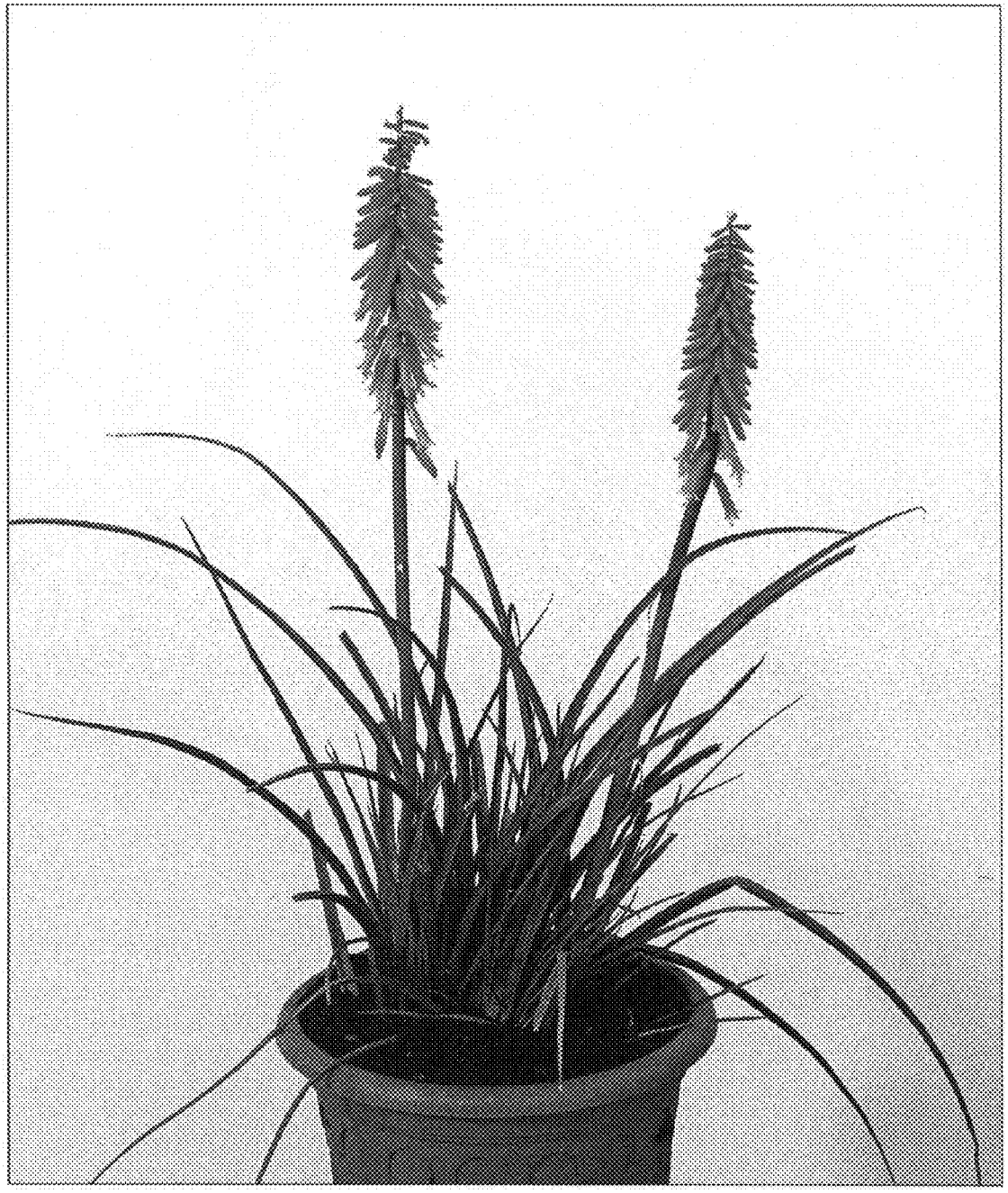

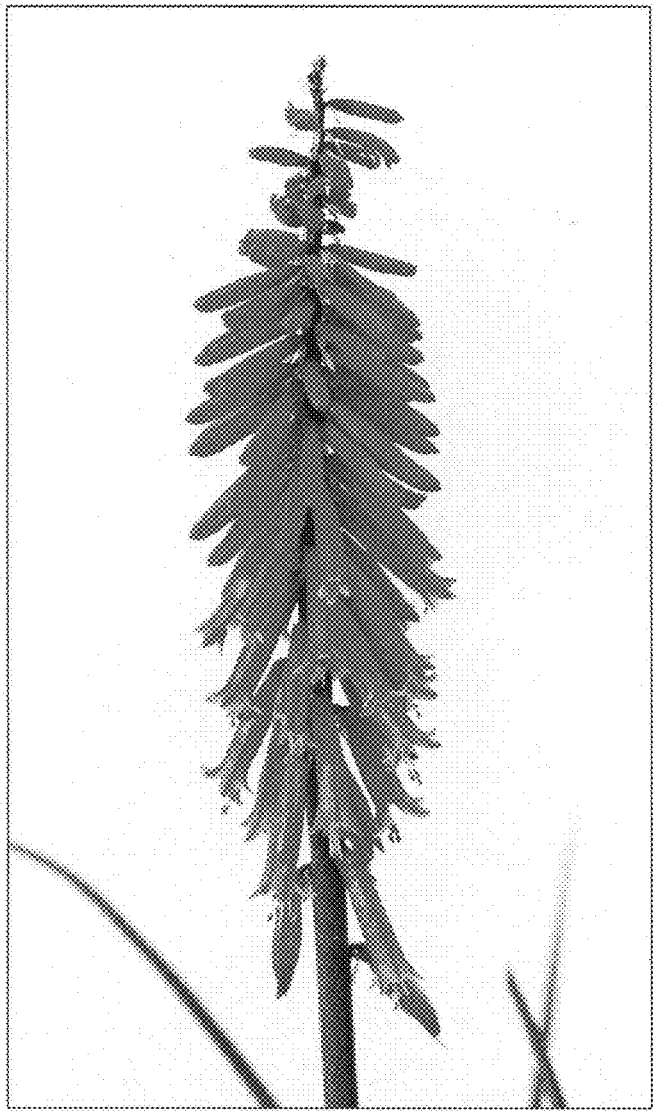
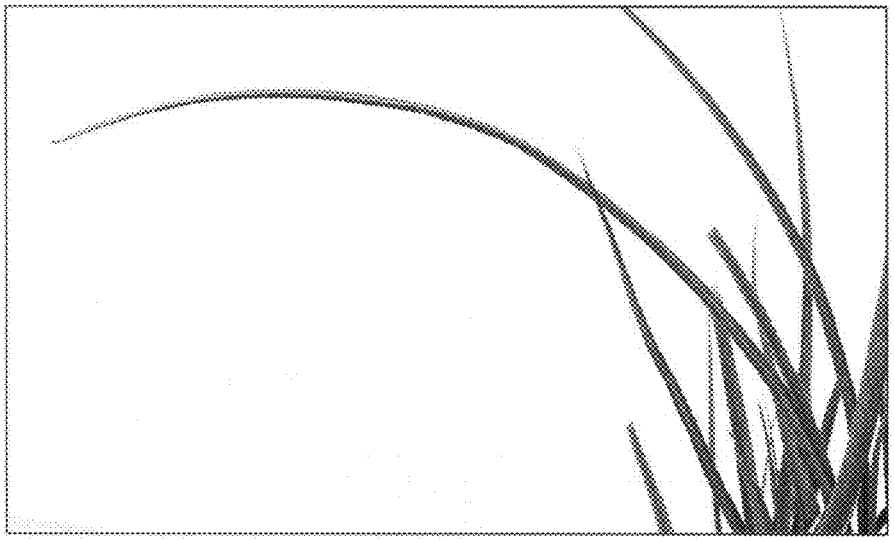

* * * * *